US00PP12616P2

(12) United States Plant Patent

Yates

(10) Patent No.: US PP12,616 P2
(45) Date of Patent: May 7, 2002

(54) SUTERA PLANT NAMED 'YASFLOS'

(76) Inventor: Frederic Yates, Poplar Nursery Holmes Chapel Rd., Somerford, Congleton, Cheshire (GB), CW12 4 FP ( * ) Notice: Subject to any disclaimer, the term of this patent is extended or adjusted under 35 U.S.C. 154(b) by 0 days.

(21) Appl. No.: 09/689,356

(22) Filed: Oct. 12, 2000

(51) Int. Cl.[7] ..... A01H 5/00

(52) U.S. Cl. ..... Plt./263

(58) Field of Search ..... Plt./263

(56) References Cited

PUBLICATIONS

UPOV–ROM GTITM Computer Database, 2001/02, GTI Jouve Retrieval Software, citation for 'Yasflos'.*

* cited by examiner

*Primary Examiner*—Bruce R. Campell
*Assistant Examiner*—Susan B. McCormick
(74) *Attorney, Agent, or Firm*—Mark P. Bourgeois

(57) ABSTRACT

A new cultivar of Sutera plant named 'Yasflos' that is characterized by vigorous growth, a bushy cascading habit and free-flowering, numerous large blue flowers, making 'Yasflos' distinct from all other existing varieties of Sutera known to the inventor.

2 Drawing Sheets

BACKGROUND OF THE INVENTION

The present invention relates to a new and distinct cultivar of Sutera known botanically as Sutera and referred to hereinafter by the cultivar name 'Yasflos'. It is a cross between two parent seedlings, both *Sutera cordata* (not patented). The seed parent is *Sutera cordata* (not patented) and the pollen parent is *Sutera cordata* (not patented). The new Sutera was selected from a long term breeding program designed to produce new patio plants and hanging baskets. The inventor conducted the first crosses in a cultivated area of Congleton, Chesire England in 1998. 'Yasflos' was selected by the inventor in 1998 as a container plant suitable for temperate climates.

'Yasflos' was selected for the specific traits of vigorous growth, free-flowering, bushy cascading habit and numerous large bluish flowers. The combined characteristics of the new invention 'Yasflos' are unique and make 'Yasflos' a distinct hanging basket Sutera, setting it apart from all other existing varieties known to the inventor. The closest comparison variety is Sutera 'Lavender Showers' (unpatented). In comparison 'Yasflos' exhibits larger, more abundant flowers that are darker in color with more blue than those of 'Lavender Showers' (unpatented).

The first asexual propagation was conducted by the inventor in the summer of 1998 in a cultivated area of Congleton, Chesire, United Kingdom, using cuttings. In vegetative propagation, 'Yasflos' has remained true to type and been found stable in successive generations.

SUMMARY OF THE INVENTION

The following traits have been repeatedly observed and represent the characteristics of the new cultivar. 'Yasflos' is selected as a new basket Sutera, for its vigorous and rapid growth, free-flowering, bushy cascading habit and numerous large blue flowers. Compared to Sutera 'Lavender Showers' (unpatented), the flowers of 'Yasflos' are larger, more abundant and darker in color with more blue than lavender. These attributes in combination distinguish this cultivar from all other existing varieties known to the inventor.

BRIEF DESCRIPTION OF THE DRAWINGS

The accompanying color photographs illustrate the overall appearance of the new cultivar.

The photo on sheet 1 is a good depiction of the entire plant showing foliage, flower presentation, color and plant habit.

The upper photo on sheet 2 is a close-up of the 'Yasflos' flower.

The lower photo on sheet 2 compares 'Lavender Showers' (unpatented) on the left to the foliage and flowers of 'Yasflos' on the right. All photographs are taken of plants grown in one-gallon containers. The prints are made using conventional photographic techniques and although colors may appear different from actual colors due to light reflectance, they are as accurate as possible by conventional photography.

BOTANICAL DESCRIPTION OF THE PLANT

The following is a detailed description of the new cultivar as grown in a one-gallon container under greenhouse conditions in Encinitas Calif. Phenotypic differences may be observed with variations in environmental, climatic and cultural conditions. The color determinations are in accordance with The Royal Horticultural Society Colour Chart, except where general color terms of ordinary dictionary significance are used.

Botanical classification: *Sutera cordata* 'Yasflos'.
Species: Cordata.
Common name: Sutera.
Parentage: The parents of Sutera 'Yasflos' are the following:
*Seed parent.*—*Sutera cordata.*
*Pollen parent.*—*Sutera cordata.*
Propagation: Vegetative cuttings.
Type: Annual for patio container or hanging basket.
Root system: Fibrous.
Special growing requirements: Grow cool 5–10° Centigrade to encourage compact growth, and water sparingly in winter.
Diseases and pests: Normal tolerance of pests and disease.

Plant habit: Cascading and bushy.
Height: 7.5 cm high above basket and 60 cm down from top of basket.
Hardiness: Half hardy in Northern Europe; will tolerate up to 30° C. at least, but not tested beyond. Appropriate for temperate regions.
Stem shape: Cylindrical.
Stem color: 147B.
Stem size: 2 mm wide and 20–40 cm long.
Internode length: 1 to 2.5 cm between nodes.
Stem surface: Pubescent, short soft straight hairs.
Foliage:
*Leaf arrangement.*—Opposite.
*Leaf division.*—Simple.
*Shape.*—Oblanceolate or elliptic.
*Base.*—Cuneate.
*Apex.*—Acute.
*Venation.*—One mid-vein.
*Margins.*—Moderately serrate.
*Surface.*—Pubescent.
*Length.*—1.50 cm long.
*Width.*—75 cm wide.
*Color upper surface* (*mature leaf*).—147A.
*Color lower surface* (*mature leaf*).—147B.
*Color upper surface* (*young leaf*).—146A.
*Color lower surface* (*young leaf*).—146.A.
*Petiole.*—2 mm long and 1 mm wide.
*Petiole surface.*—Pubescent.
Flower:
*Type.*—Singly born in axials.
*Shape.*—Circular or rotate.
*Arrangement.*—One per flower cluster.
*Surface.*—Glabrous.
*Fragrance.*—Faint honeysuckle scent.
*Flower size.*—1 cm high and 1.50 cm in diameter.
*Flowering season.*—Spring and summer.
*Flowering time.*—Diurnal.
*Aspect.*—Flowers facing outward.
*Peduncle length.*—1.50 cm long.
*Peduncle width.*—0.50 cm wide.
*Peduncle color.*—138C.
*Persistent or non-persistent.*—Persistent.
*Petals.*—Five petals.
*Fused or unfused.*—Fused.
*Petal color.*—88C.
*Color of throat.*—13B.
*Depth of throat.*—6 mm deep.
*Calyx.*—Polysepalous with five segments.
*Calyx size.*—4 mm wide by 2 mm high.
*Calyx color.*—138A.
Reproduction organs:
*Anther shape.*—Longitudinal.
*Anther color.*—16A with brown edge 166A.
*Stamen.*—Four in number, arranged in two pairs.
*Stamen dimensions.*—One pair is 3 mm in length and 0.25 mm in diameter and the other pair is 5 mm in length and 0.25 mm in diameter.
*Stamen.*—Polleniferous.
*Pistil.*—One.
*Pistil color.*—145A.
*Pistil dimensions.*—6 mm in length an 0.50 mm in diameter.
*Pollen color.*—16A.
Seed production:
*Capsule shape.*—Ovate in shape.
*Capsule color.*—200A.
*Capsule dimensions.*—4 mm in length and 1.5 mm in diameter.
*Seed shape.*—Ovate in shape.
*Seed color.*—200A.
*Seed dimensions.*—1.0 mm in length and 0.6 mm in diameter.
*Seed quantity.*—12 per capsule.

I claim:

1. A new and distinct cultivar of *Sutera cordata* plant named 'Yasflos' as herein described and illustrated.

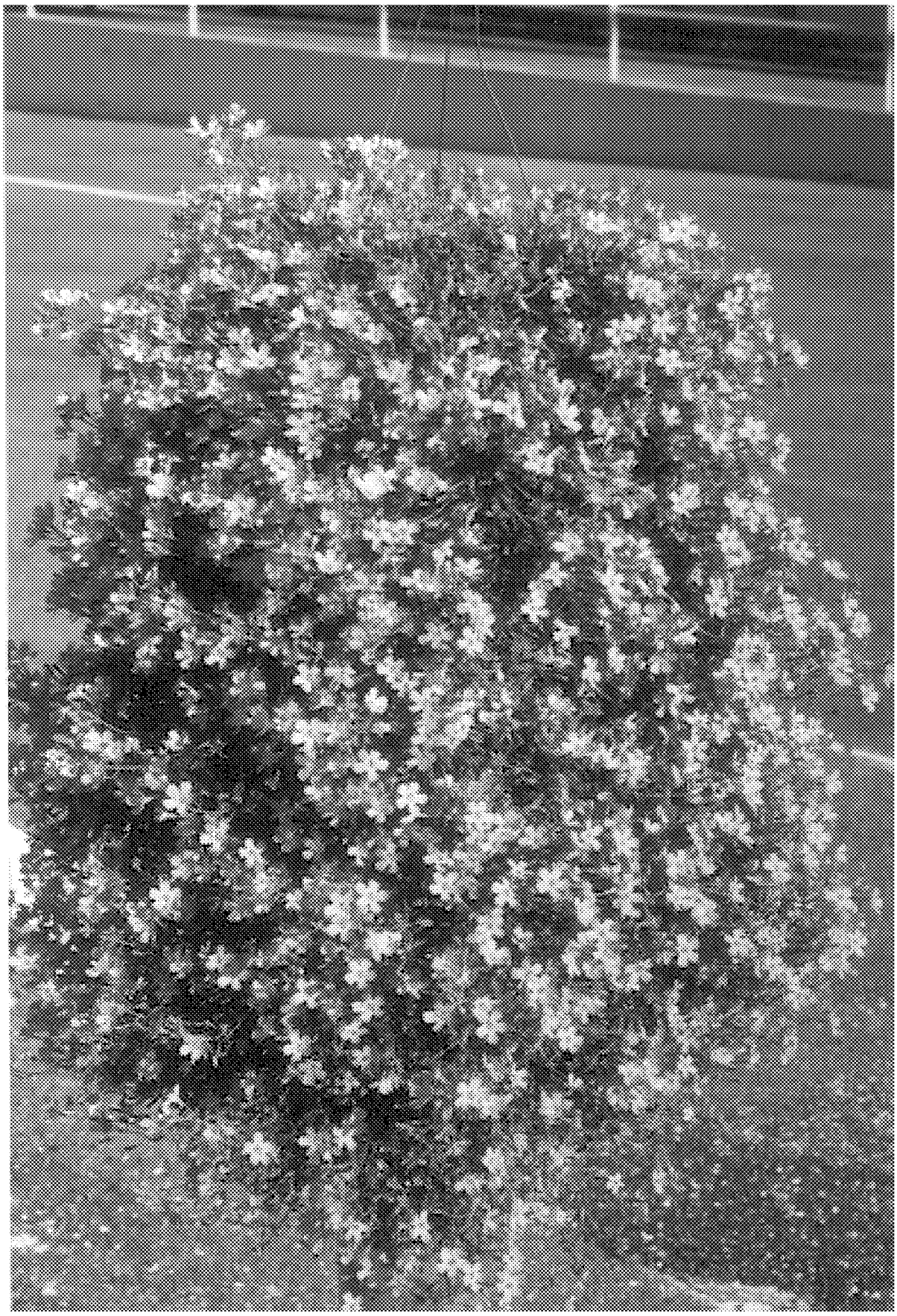

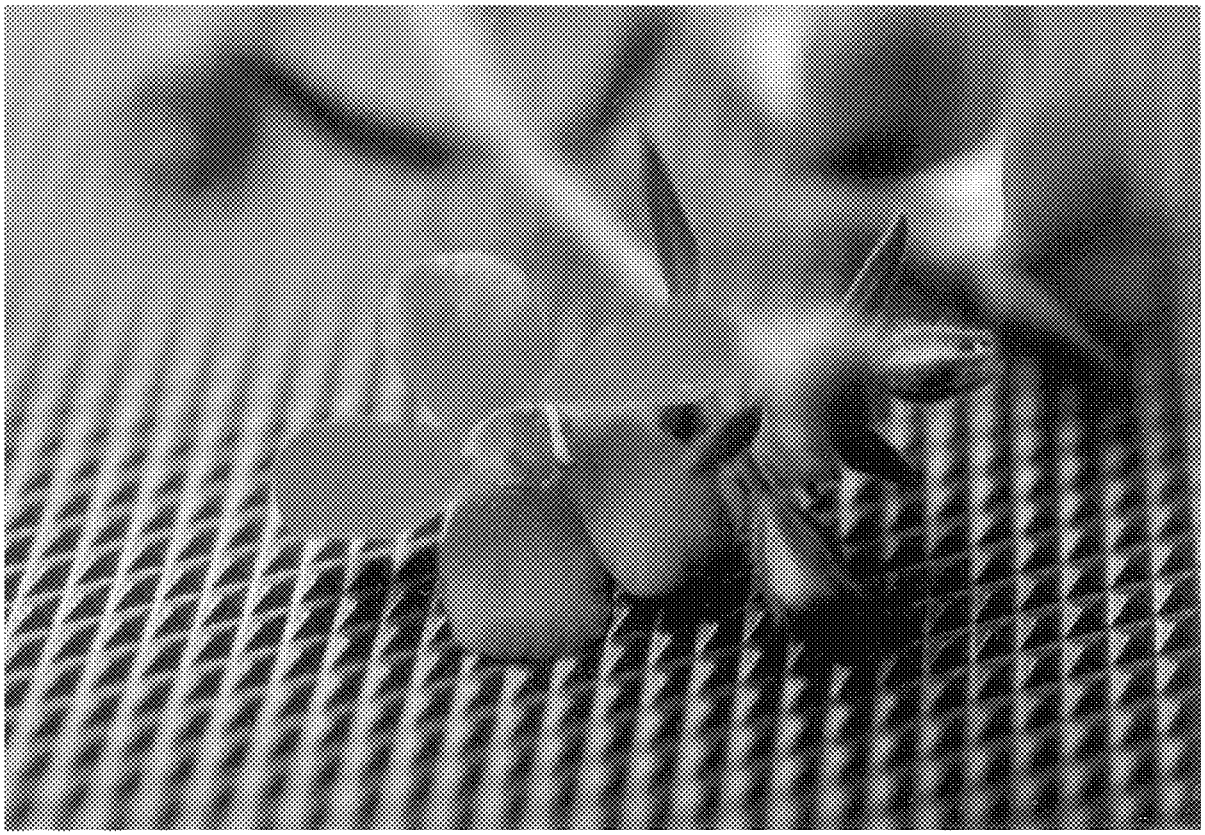
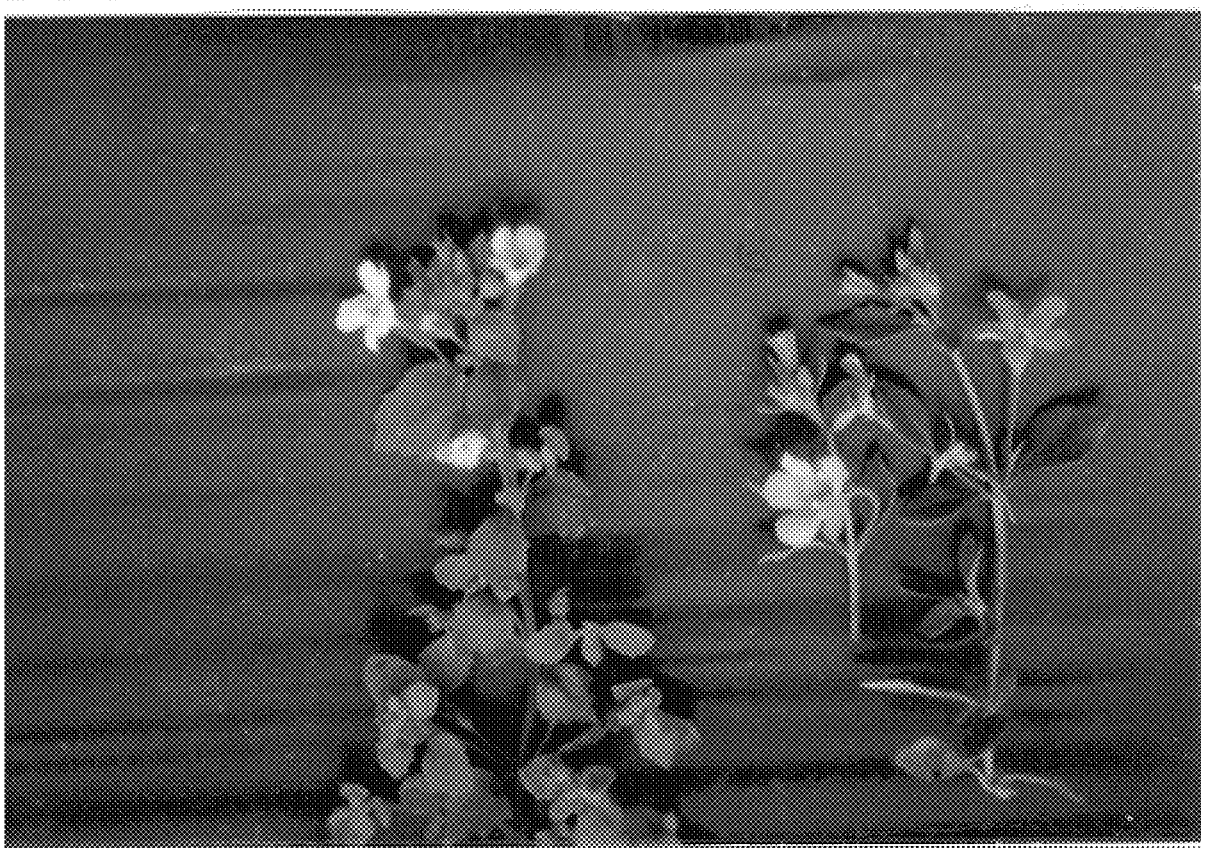

* * * * *